United States Patent [19]

Hardies

[11] 4,152,516

[45] May 1, 1979

[54] 1-(3-ALKYL- OR -ALKARYL-4-H-ALKYL- OR -ARYL-5-ISOTHIAZOLYL)-2-OXO-3,5-DIMETHYLHEXAHYDRO-1,3,5-TRIAZINES

[75] Inventor: Donald E. Hardies, Wadsworth, Ohio

[73] Assignee: PPG Industries, Inc., Pittsburgh, Pa.

[21] Appl. No.: 876,453

[22] Filed: Feb. 9, 1978

[51] Int. Cl.$^2$ ............................................. C07D 251/08
[52] U.S. Cl. ............................................. 544/220; 71/90
[58] Field of Search ............................................. 544/220

[56] References Cited

U.S. PATENT DOCUMENTS

| 3,563,985 | 2/1971 | Volpp et al. | 260/247.1 |
|---|---|---|---|
| 3,696,101 | 10/1972 | Litt et al. | 260/248 NS |
| 3,705,155 | 12/1972 | Miller | 260/248 NS |
| 3,849,412 | 11/1974 | Krenzer | 260/248 NS |
| 3,860,593 | 1/1975 | Krenzer | 260/248 NS |
| 4,020,065 | 4/1977 | Rathgeb | 544/220 |

FOREIGN PATENT DOCUMENTS 1045412  10/1966  United Kingdom ..................... 544/220

OTHER PUBLICATIONS

Clemens et al., *J. of Org. Chem.*, vol. 26, pp. 767-769 (1961).

*Primary Examiner*—John M. Ford
*Attorney, Agent, or Firm*—Robert J. Grassi

[57] ABSTRACT

Disclosed are compositions of 1-(3-alkyl-, or 3-alkaryl-, 4-H-, or 4-alkyl, or 4-aryl-5-isothiazolyl)-2-oxo-3,5-dimethylhexahydro-1,3,5-triazines, such as 1-(3-methyl-5-isothiazolyl)-2-oxo-3,5-dimethylhexahydro-1,3,5-triazine, and their use for controlling weeds, such as jimsonweed.

7 Claims, No Drawings

1-(3-ALKYL- OR -ALKARYL-4-H-ALKYL- OR -ARYL-5-ISOTHIAZOLYL)-2-OXO-3,5-DIMETHYL-HEXAHYDRO-1,3,5-TRIAZINES

BACKGROUND OF THE INVENTION a. Field of the Invention

The invention concerns 1-(isothiazolyl)-1,3,5-triazines, particularly 1-(substituted isothiazolyl)-2-oxo-1,3,5-triazine; for example 1-(3-methyl-5-isothiazolyl)-2-oxo-3,5-dimethylhexahydro-1,3,5-triazine, and the method of controlling weeds, such as jimsonweed with the compositions.

b. Description of the Prior Art

Control of undesirable plants (weeds) by chemicals requires the discovery of compounds which interact with the complex biochemical system of the plant so as to cause death or retardation of plant growth. Only a relatively small amount of the millions of known chemical compounds control weeds.

This is shown by the prior art concerning triazines and isothiazoles for nothing therein suggests or teaches the compositions of this invention or the method of controlling weeds with the compositions of this invention. For example, U.S. Pat. No. 3,563,985 discloses the formation of isothiazoles having an urea, carbamate, or thiocarbamate attached to the 3 or 5 position of the isothiazole ring. U.S. Pat. No. 3,860,593 discloses compounds of substituted thiadiazole substituted triazines such as 1-(5-isopropyl-1,3,4-thiadiazol-2-yl)-3-methyl-5-benzylhexahydro-1,3,5-triazine-2-one. U.S. Pat. No. 3,849,412 discloses substituted thiadiazol substituted -1,3,5-triazineones, such as 1-(5-isopropyl-1,3,4-thiadiazol-2-yl)-3,5-dimethylhexahydro-1,3,5-triazine-2-one. U.S. Pat. No. 3,705,155 discloses substituted 1-thiadiazoylhexahydro-1,3,5-triazine-2-ones, such as 1-(1,2,4-thiadiazol-5-yl)-3,5-dimethylhexahydro-1,3,5-triazine-2-one. U.S. Pat. No. 3,696,101 discloses substituted tetrahydrobenzothiazolyl-substituted hexahydro-2-triazines, such as 1-(2-[5,5,7-trimethyl]-4,5,6,7-tetrahydrobenzothiazolyl)-2-oxo-3,5-dimethylhexahydro-1,3,5-triazine. D. H. Clemens et al., *Journal of Organic Chemistry*, 26, pages 767–769 (1961), describes the reactions of isocyanates and isothiocyanates with azomethines to form triazones and thiotriazones.

SUMMARY OF THE INVENTION

The invention concerns compositions of the general formula:

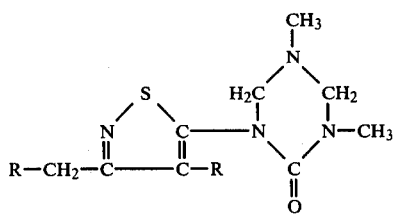

wherein

R is hydrogen, methyl, ethyl, n-propyl, phenyl, p-chlorophenyl, or p-nitrophenyl; such as 1-(3-methyl-5-isothiazolyl)-2-oxo-3,5-dimethylhexahydro-1,3,5-triazine, and it also concerns the method of controlling weeds, particularly broadleaf weeds such as jimsonweed.

DESCRIPTION OF THE PREFERRED EMBODIMENTS

The useful compositions of this invention are represented by the general formula (I):

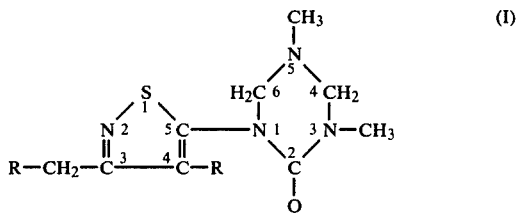

wherein

R is hydrogen, methyl, ethyl, n-propyl, phenyl, p-chlorophenyl, or p-nitrophenyl.

Representative examples of which are:

1-(3-methyl-5-isothiazolyl)-2-oxo-3,5-dimethylhexahydro-1,3,5-triazine;

1-(3-ethyl-4-methyl-5-isothiazolyl)-2-oxo-3,5-dimethylhexahydro-1,3,5-triazine;

1-(3-n-propyl-4-ethyl-5-isothiazolyl)-2-oxo-3,5-dimethylhexahydro-1,3,5-triazine;

1-(3-n-butyl-4-n-propyl-5-isothiazolyl)-2-oxo-3,5-dimethylhexahydro-1,3,5-triazine;

1-(3-benzyl-4-phenyl-5-isothiazolyl-)-2-oxo-3,5-dimethylhexahydro-1,3,5-triazine;

1-(3-p-chlorobenzyl-4-p-chlorophenyl-5-isothiazolyl)-2-oxo-3,5-dimethylhexahydro-1,3,5-triazine; and 1-(3-p-nitrobenzyl-4-p-nitrophenyl-5-isothiazolyl)-2-oxo-3,5-dimethylhexahydro-1,3,5-triazine.

The compounds 1-(3-methyl-5-isothiazolyl)-2-oxo-3,5-dimethylhexahydro-1,3,5-triazine, 1-(3-ethyl-4-methyl-5-isothiazolyl)-2-oxo-3,5-dimethylhexahydro-1,3,5-triazine, 1-(3-n-propyl-4-ethyl-5-isothiazolyl)-2-oxo-3,5-dimethylhexahydro-1,3,5-triazine, and 1-(3-benzyl-4-phenyl-5-isothiazolyl)-2-oxo-3,5-dimethylhexahydro-1,3,5-triazine are especially preferred, with 1-(3-methyl-5-isothiazolyl)-2-oxo-3,5-dimethylhexahydro-1,3,5-triazine being the most preferred.

The compounds are generally synthesized by the formation of the appropriate isothiazole (II) by the following steps of Reaction A, according to the procedure in U.S. Pat. No. 2,871,243. In some cases, the intermediate may readily hydrolyze and are then best isolated as a salt which in turn is neutralized before oxidation to the corresponding substituted 5-aminoisothiazole (II).

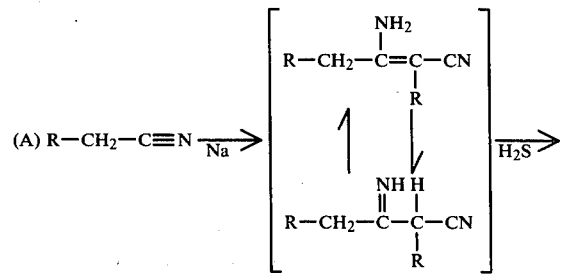

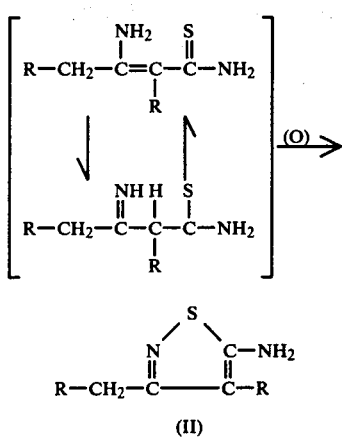

The appropriate isothiazole (II) is then reacted with methylisocyanate (CH₃NCO) to form the appropriate urea of general formula (IV) as shown by reaction B, described in U.S. Pat. No. 3,454,591.

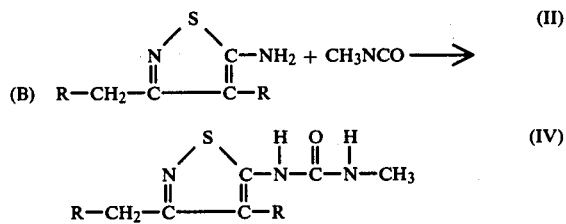

The urea of general formula (IV) is then reacted with formaldehyde and methylamine according to reaction C, to form the composition of general formula (I).

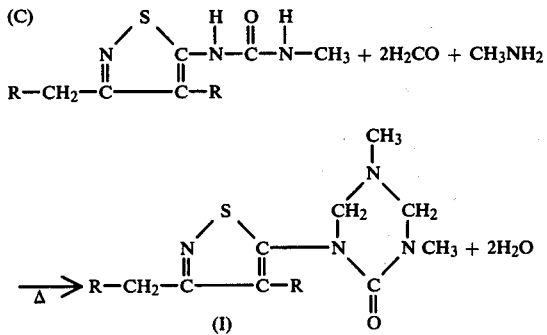

The following examples illustrate the synthesis of the compounds of this invention.

EXAMPLE I a. Synthesis of N-(3-methyl-5-isothiazolyl)-N'-methylurea

5-Amino-3-methylisothiazole was obtained from its hydrochloride salt by treating the hydrochloride salt with 1N NaOH solution and extracting with ether. Tetrahydrofuran was distilled from calcium hydride.

The procedure described in U.S. Pat. No. 3,454,591 was followed.

Methylisocyanate (1.96 milliliters, 0.04 mole) was added dropwise to a thirty (30) milliliter solution of the distilled tetrahydrofuran containing the above mentioned 5-amino-3-methylisothiazole (5.0 grams, 0.04 mole), and then the resulting yellow solution was refluxed for 3 hours, during which time a white precipitate formed. The solution was cooled and filtered, giving 3.73 grams of N-(3-methyl-5-isothiazolyl)-N'-methylurea, also referred to as 3-methyl-5-N-methylureidoisothiazole.

b. Synthesis of 1-(3-Methyl-5-isothiazolyl)-2-oxo-3,5-dimethylhexahydro-1,3,5-triazine The synthesized N-(3-methyl-5-isothiazolyl)-N'-methylurea (4.34 grams, 0.027 mole) was added to a 100 milliliter round bottom flask containing eight (8) milliliters of thirty-seven percent (37%) aqueous formaldehyde and twenty-five (25) milliliters of dimethylformamide (DMF). The solution was stirred during the addition and then for an additional 30 minutes. Four (4) milliliters of forty percent (40%) aqueous methylamine was added dropwise to the stirred solution over a period of thirty (30) minutes and stirring was continued for about 14 hours at ambient temperature. The resulting precipitate (1.81 grams) of 5-methyl-7-(N-methylcarbamoyl)-3-methylisothiazolo[5,4-d]-4,5,6,7-tetrahydropyrimidine was removed by filtration. The mother liquor from the filtration was collected, and the solvent was removed by vacuum, leaving a light tan solid (4.05 grams). Two grams of this solid were dissolved in ethanol and evaporated onto alumina (neutral grade III) and placed on top of a 1×12 inch column of 70–290 mesh alumina (neutral grade III) wet packed with carbon tetrachloride. The column was eluted with a solvent mixture of carbon tetrachloride and ethyl acetate having a volume ratio of one to one, and 20 milliliter fractions were collected. Fractions (11–15) were collected and the solvent was evaporated from these fractions to yield a whitish powder which was recrystallized from the solvent mixture to yield a white powder of 1-(3-methyl-5-isothiazolyl)-2-oxo-3,5-dimethylhexahydro-1,3,5-triazine (1.0 gram). This had a melting point of 161°–164° C. Its infrared spectra (mull) had the following absorption bands: $v_{CH}$ (aliphatic) at 2850–2980 centimeter$^{-1}$, $v_{(C=O)}$ at 1655 centimeter$^{-1}$, and it had nuclear magnetic resonance signals ((NMR) in (CDCL₃)) of a singlet (3H) at 2.36δ (CH₃), singlet (3H) at 2.63δ (CH₃), singlet (3H) at 2.98δ (CH₃), singlet (2H) at 4.27δ (—CH₂—), singlet (2H) at 4.66δ (—CH₂—), and singlet (1H) at 6.25δ [4-H(isothiazole)].

UTILITY AND APPLICATION OF THE COMPOSITIONS a. Manner of Applications and Weeds Controlled

Undesirable plants, weeds, primarily broadleaf and grassy weed species, are effectively controlled according to this invention by the use of the compounds of general formula (I), usually by contacting the weeds with a herbicidal amount of the compound. The control can be by application of one or more of the compounds to the soil or weed (e.g., the weed environment) either prior to (preemergence) or after emergence (postemergence) of the weed, or in any combination thereof, but the preferred method is to contact the weed after emergence of the weeds from the seeds (postemergence). If both crop plants and weeds are emerging, then the compound is applied after emergence of both. A preferred method is to contact the foilage of the weed with a lethal dosage of one or more of the compounds. This may be readily achieved by applying the compound itself, but preferably it is applied in the form of a suitable agricultural composition to the foilage of the weed. The lethal (herbicidal) dosage may vary with the plant size, plant species, and/or weather. A workable lethal dosage for plant contact is from 0.25 to 500 pounds per acre (0.27 to 550 kilograms/hectare) of one or more of the compounds whether applied by itself or in the form of an agricultural composition, while from 0.25 to 50 pounds per acre (0.27 to 55 kilograms/hectare) is normally the range to use under various conditions, but preferably from 1 to 10 pounds per acre (1.1 to 11 kilograms/hectare) under optimum conditions.

It has been discovered that the compounds of the general formula (I), such as 1-(3-methyl-5-isothiazolyl)-2-oxo-3,5-dimethylhexahydro-1,3,5-triazine are particularly effective against weeds (undesirable plants), such as broadleaf weeds and grassy weeds, but particularly against broadleaf weeds. The compounds are effective particularly against weeds of the genera: *Brassica, Echinochloa, Abutilon, Datura, Ipomoea, Sesbania, Xanthium,* and *Gossypium* and their equivalents. The compounds were found extremely effective against the species: *Brassica kaber,* D.C. (wild mustard), *Echinochloa crusgalli* (barnyardgrass), *Datura stramonium* (jimsonweed), *Ipomoea spp.* (morningglory), *Abutilon theophrasti* (velvetleaf), *Sesbania spp.* (coffeeweed), *Xanthium pensylvanicum* (common cocklebur), and *Gossypium hirsutum* (cotton).

The following Example illustrates a manner in which this invention may be practiced.

The effectiveness of the compounds of general formula (I) as herbicides for controlling weeds is illustrated in this Example which uses 1-(3-methyl-5-isothiazolyl)-2-oxo-3,5-dimethylhexahydro-1,3,5-triazine in a postemergence application.

The mixture of weed seeds was a representative cross-section of broadleaf and grassy weeds, and contained seeds from species of each of the following genera: *Brassica, Echinochloa, Abutilon, Datura, Ipomoea, Sesbania, Xanthium,* and *Gossypium.* The particular weed species were: *Brassica kaber,* D.C. (wild mustard), *Echinochloa crusgalli* L. Beauv. (barnyardgrass), *Datura stramonium* (jimsonweed), *Ipomoea spp. (morning-glory), Abutilon theophrasti* (velvetleaf), *Sesbania spp.* (coffeweed), *Xanthium pensylvanicum* (common cocklebur), and *Gossypium hirsutum* (L.) Coker variety (cotton).

PROCEDURE

Screened top soil which had been limed to a pH of 6.5 and had been fertilized with 12-12-12 farm grade fertilizer at a rate of about seventy-five (75) pounds per acre of total nitrogen, was placed in plastic two and three-quarter (2.75) inch square pots to a depth of about two and five-tenths (2.5) inches. Single weed species were grown per pot, by placing the seeds of a single weed species on top of the soil in the pot, and covering them with one-quarter (¼) inch of soil. The number of seeds of a weed species per pot varied from about eight (8) to forty (40) depending upon the particular weed species grown in the pots. The weed species were planted according to a growth cycle to insure that at the time of postemergence testing of the compounds, that the weed plant emerging had at least one true leaf, e.g., cocklebur was planted prior to weedy grasses such as barnyardgrass. The pots after being seeded were watered and placed in the laboratory growth room where the weeds were grown under artificial light from Gro-Lux ® fluorescent lights at a temperature of about 23°–33° C. and a relative humidity of 50 to 80 percent, until the emerging plants had several true leaves.

The test compound was dissolved in a standard solvent mixture of acetone, methanol, dimethylformamide (90:8:2 volume/volume) and was applied postemergence to the leaves at the rate of 482 milligrams of the test compound per 4.63 square feet which is equivalent to 10 pounds of active ingredient per surface acre (10 lbs. ai/acre), by means of a herbicidal sprayer. The sprayer was equipped with a Tee-Jet 8001 spray nozzle tip and the sprayer operated in the range of 35–40 pounds per square inch pressure with compressed air. The sprayer was set to deliver fifty (50) gallons of solution per surface acre.

The potted plants, which had at least one true leaf, were placed on a tray, and the tray was placed on a conveyor belt which passed through the sprayer at about nine-tenths (0.9) foot per second. The tray tripped a microswitch which activated a solenoid valve to release the spray solution containing the test compound.

Immediately after the spray treatment, the sprayed pots of weeds were transferred to the above mentioned growth room and held there for visual observations of the weeds. Daily observations were made for interim changes in the weeds and a final observation was made fourteen (14) days after the postemergence spray treatment. This final observation included abnormal physiological changes; such as: stem bending, petiole curvature, epinasty, hyponasty, retardation, stimulation, root development, necrosis, and retarded growth regulant characteristics.

These observations were reported as injury ratings based on a relative scale of zero (0) to ten (10); zero (0) meaning no observed injury or control, and ten (10) meaning severe injury resulting in complete control, all plants were killed. The abnormal physiological ratings were reported as necrosis (Ne), chlorosis (Cl), retardation (R), and no visual abnormal responses, zero (0).

EXAMPLE II

When 1-(3-methyl-5-isothiazolyl)-2-oxo-3,5-dimethylhexahydro-1,3,5-triazine from Example I was applied postemergence at 10 pounds of active ingredient per acre (11.0 kilograms/hectare) according to the procedure described above, the following results shown in Table I were obtained.

Column 1 of Table I gives the weed species, both its scientific and common name, and Column 2 gives the control rating and the physiological response obtained.

TABLE I

POSTEMERGENCE CONTROL AT 10 POUNDS OF ACTIVE INGREDIENT/ACRE OF 1-(3-METHYL-5-ISOTHIAZOLYL)-2-OXO-3,5-DIEMTHYLHEXAHYDRO-1,3,5-TRIAZINE

| Weed Species | Control Rating | Abnormal Response |
|---|---|---|
| *Xanthium pensylvanicum* L. common cocklebur | 10 | Necrosis |
| *Datura stramonium* (L.) jimsonweed | 10 | Necrosis |
| *Brassica kaber* (D.C.) wild mustard | 10 | Necrosis |
| *Gossypium hirsutum* (L.) (Coker Variety) cotton | 9 | Necrosis |
| *Sesbania* spp. coffeeweed | 9 | Necrosis |
| *Abutilon theophrasti* (L.) velvetleaf | 10 | Necrosis |

TABLE I-continued
POSTEMERGENCE CONTROL AT 10 POUNDS OF ACTIVE INGREDIENT/ACRE OF 1-(3-METHYL-5-ISOTHIAZOLYL)-2-OXO-3,5-DIEMTHYLHEXAHYDRO-1,3,5-TRIAZINE

| Weed Species | Control Rating | Abnormal Response |
|---|---|---|
| *Ipomoea* spp. morningglory | 9 | Necrosis |
| *Echinochloa crusgalli* (L.) Beauv. barnyardgrass | 6 | Necrosis |

These test results illustrate the herbicidal activity against weeds of the compounds of general formula (I), and, in particular, broadleaf weeds. Although the lethal dosage or herbicidally effective amount shown was for 10 pounds per acre (11 kilograms/hectare), such a dosage can be varied from 0.25 to 200 pounds per acre (0.27 to 220 kilograms/hectare), depending upon the weed species, the age of the weeds, and the weather, but generally 0.25 to 50 pounds per acre will suffice, and under optimum conditions 0.25 to 10 pounds per acre is preferred.

b. Use of Formulations

Although the plants may be contacted with 1-(3-methyl-5-isothiazolyl)-2-oxo-3,5-dimethylhexahydro-1,3,5-triazine itself or with the other compounds disclosed herein, as directly synthesized, or as granules, it is preferable to use other suitable agricultural formulations which contain other ingredients which enhance application of the compound or compounds. These agricultural formulations will generally comprise from 5 to 95 percent by weight of 1-(3-methyl-5-isothiazolyl)-2-oxo-3,5-dimethylhexahydro-1,3,5-triazine, or of the other compounds disclosed herein, singularly or as a mixture of the compounds of general formula (I). The other ingredients of these formulations will be from 1 to 95 percent by weight of an agricultural diluent, or from 1 to 20 percent by weight of a surface active agent or other ingredients required to produce wettable powders, dusts, solutions, emulsifiable concentrates, granules, and the like or both.

Wettable powders will contain from 25 to 80 percent active ingredients, from 0.1 percent to 5.0 percent wetters and dispersants with the balance consisting of inorganic absorptive diluents.

Since the compounds are solids, they may be dissolved in one or more solvents and then sprayed upon the absorptive diluents of attapulgite clay, synthetic fine silica, and synthetic calcium and sodium alumino-silicates, or other solid insecticides, or foliar fungicides mentioned herein and in some cases the solvent or solvents may be evaporated off.

Emulsifiable oils will contain from 20 percent to 97 percent active ingredient, from 3.0 to 10.0 percent of an emulsifying agent, and may also contain from 1 percent to 77 percent solvent or mixture of solvents.

Granules will contain from 5 percent to 25 percent active ingredient extended upon a granular base such as vermiculite or granular attapulgite. Granules produced by extrusion or tumbling or will contain like amounts of active ingredients.

Dusts are mixtures of the active compound with finely divided solids such as talc, attapulgite clay, kieselguhr, and other organic and inorganic solids which act as dispersants and carriers for the compound. The finely divided solids have an average particle size of less than about 50 microns. A typical dust formulation will contain from 1.0 to 10.0 parts by weight of 1-(3-methyl-5-isothiazolyl)-2-oxo-3,5-dimethylhexahydro-1,3,5-triazine or in mixture with the other compounds of general formula (I) to 99.0 to 90.0 parts by weight of talc.

Wettable powders for preemergent or postemergent application are finely divided solid particles, which disperse readily in water or other liquids. The wettable powder is applied to the soil, seed, or plant as a dry dust or as a water or other liquid emulsion.

Typical wettable powder carries are Fuller's earth, Kaolin clays, silicas, and other highly absorbent, readily wet, inorganic diluents. Wettable powders normally contain about 5 to 80 weight percent of the active ingredient, depending on the absorbency of the carrier, and usually contain a small amount of a wetting, dispersing, or emulsifying agent to facilitate dispersion.

For example, a useful wettable powder formulation comprises by weight about 80.8 parts of one or more of the compounds of general formula (I), 17.9 parts of Palmetho clay, and 1.0 part of sodium lignosulfate and 0.3 parts of sulfonated aliphatic polyester as wetting agents.

Other postemergent formulations are emulsifiable concentrates. These are homogeneous liquid or paste compositions which are dispersible in water or other liquids. They may consist entirely of one or more of the compounds of general formula (I) and a liquid or solid emulsifying agent, or they may also contain a liquid carrier, such as xylene, heavy aromatic naphthas, or other non-volatile organic solvents. These emulsifiable concentrates are dispersed in a liquid carrier, e.g., water, and generally are applied as a spray to the area or plant to be treated. The weight percent of the compounds of general formula (I) in these concentrates varies with the manner of application, but generally is from 0.5 to 95 percent.

Representative wetting, dispersing, and emulsifying agents for the agricultural formulations are alkyl and alkylaryl sulfonates and sulfates, and their alkali salts; polyethylene oxides, sulfoxided oils, fatty acid esters of polyhydric alcohols, and other surface-active agents, e.g., TWEEN 20 ®, a commercial surfactant. If used, the surfactant would vary from 0.25 to 15 weight percent of the composition.

Other formulations for herbicidal applications include simple solutions of the compound in solvents in which it is completely soluble at the desired concentration, e.g., acetone or other organic solvents; aerial spray formulations comprising relatively coarse particles coated with the compounds of general formula (I), and pressurized spray formulations such as aerosols, which use low boiling dispersant solvents such as Freon. All of these formulations may be used to apply the active compound to the area to be treated.

These formulations may also include other agriculturally useful materials such as nematocides, pesticides, and herbicides which are non-toxic to the desired vegetation, but which are effective against other weeds, pests, and nematodes, their eggs, fungi and bacteria so that one application will serve to rid the area of several undesirable species. For example, 1-(3-methyl-5-isothiazolyl)-2-oxo-3,5-dimethylhexahydro-1,3,5-triazine may be used with sodium azide, or potassium azide in formulations which contain stabilizers for both the azide and the isothiazole compound. Other combinations of this compound are those with certain ureas, thiocarbamates, carbamates, which increase the useful herbicidal spectrum of the above mentioned triazines, reduce the number of applications required by husbandmen and others who require use of these compounds to assist the healthful growth of crops. It may be used in combination with fertilizers, particularly thosed used in foliage applications, provided of course that the composition formulation is such that the compounds of general formula (I) is not hydrolyzed, e.g., the pH conditions are maintained between 2–10.

c. Effective Amounts to Apply

Normally the effective amount of the compound to apply will vary with the environment, depending on the type of soil, the wetness of the weather, the number and type of weed species, and the time of application.

When one or more of the compounds of the general formula (I) are applied in the form of a suitable agricultural composition, the application rate of such formulation is such that the herbicidal dosage of a compound of the general formula (I) itself, or a mixture of the compounds, is between 0.25 to 500 pounds per acre (0.27 to 550 kilograms/hectare). Generally, the rate is from 0.25 to 50 pounds per acre (0.27 to 55 kilograms/hectare), normally from 0.25 to 20 pounds per acre, but preferably from 1 to 10 pounds per acre (1.1 to 11 kilograms/hectare) under optimum conditions.

Generally those compounds of 1-(3-methyl-5-isothiazolyl)-2-oxo-3,5-dimethylhexahydro-1,3,5-triazine, 1-(3-ethyl-4-methyl-5-isothiazolyl)-2-oxo-3,5-dimethylhexahydro-1,3,5-triazine, 1-(3-n-propyl-4-ethyl-5-isothiazolyl)-2-oxo-3,5-dimethylhexahydro-1,3,5-triazine, and 1-(3-benzyl-4-phenyl-5-isothiazolyl)-2-oxo-3,5-dimethylhexahydro-1,3,5-triazine are used at lower rates of about 50 pounds of the active ingredient per acre to 1 pound of the active ingredient per acre.

While the invention has been described with reference to specific details of certain illustrative embodiments, it is not intended that it shall be limited thereby except insofar as such details appear in the accompanying claims.

I claim:
1. A composition of the formula:

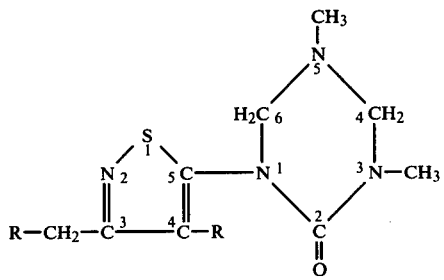

wherein
R is hydrogen, methyl, ethyl, n-propyl, phenyl, p-chlorophenyl, or p-nitrophenyl.
2. 1-(3-methyl-5-isothiazolyl)-2-oxo-3,5-dimethylhexahydro-1,3,5-triazine.
3. 1-(3-ethyl-5-methyl-5-isothiazolyl)-2-oxo-3,5-dimethylhexahydro-1,3,5-triazine.
4. 1-(3-n-propyl-4-ethyl-5-isothiazolyl)-2-oxo-3,5-dimethylhexahydro-1,3,5-triazine.
5. 1-(3-benzyl-4-phenyl-5-isothiazolyl)-2-oxo-3,5-dimethylhexahydro-1,3,5-triazine.
6. 1-(3-p-chlorobenzyl-4-p-chlorobenzyl-5-isothiazolyl)-2-oxo-3,5-dimethylhexahydro-1,3,5-triazine.
7. 1-(3-p-nitrobenzyl-4-p-nitrophenyl-5-isothiazolyl)-2-oxo-3,5-dimethylhexahydro-1,3,5-triazine.

* * * * *